United States Patent

Jensen-Korte et al.

Patent Number: 4,973,726
Date of Patent: Nov. 27, 1990

[54] HERBICIDAL 3-AMINOPYRAZOLIN-5-ONES

[75] Inventors: Uta Jensen-Korte, Duesseldorf; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 444,649

[22] Filed: Dec. 1, 1989

Related U.S. Application Data

[62] Division of Ser. No. 269,809, Nov. 10, 1988, Pat. No. 4,909,830.

[30] Foreign Application Priority Data

Nov. 17, 1987 [DE] Fed. Rep. of Germany ....... 3738963

[51] Int. Cl.$^5$ ........................................... C07C 251/06
[52] U.S. Cl. ...................................................... 558/6
[58] Field of Search ........................................... 558/6

[56] References Cited

PUBLICATIONS

Hunger et al, *Chemical Abstracts*, vol. 55 (1961), cols. 9380, 9381.

Primary Examiner—Robert W. Ramsuer
Attorney, Agent, or Firm—Sprung Horn Kramer & Woods

[57] ABSTRACT

Herbicidal 3-aminopyrazolin-5-ones of the formula

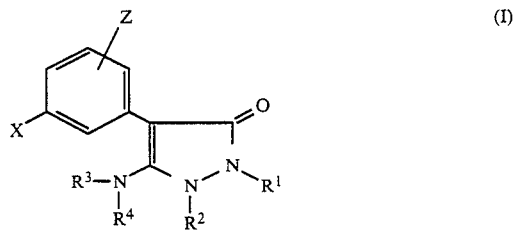

in which
R$^1$ stands for alkyl, alkenyl, halogenoalkyl, halogenoalkenyl, alkoxyalkyl, alkylthioalkyl, cycloalkyl, for optionally substituted aralkyl or for optionally substituted aryl,
R$^2$ stands for hydrogen or alkyl,
R$^3$ stands for hydrogen or alkyl,
R$^4$ stands for hydrogen, alkyl, alkenyl, alkinyl, alkoxyalkyl, alkylthioalkyl, alkoxycarbonylalkyl or alkanoyl, or
R$^3$ and R$^4$ together stand for an alkylene or alkenylene radical, each of which is divalent, X stands for halogen, alkyl, alkoxy, alkylthio, halogenoalkyl, halogenoalkoxy or halogenoalkylthio, and
Z stands for hydrogen, halogen, alkyl, alkoxy, alkylthio, halogenoalkyl, halogenoalkoxy or halogenoalkylthio, and acid addition salts thereof. Intermediates of the formula

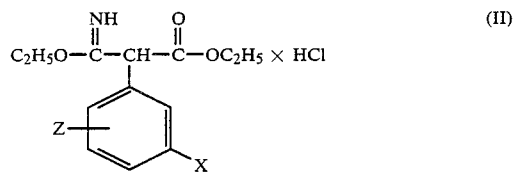

are also disclosed.

1 Claim, No Drawings

HERBICIDAL 3-AMINOPYRAZOLIN-5-ONES

This is a division, of application Ser. No. 269,809, filed Nov. 10, 1988, now pending.

The invention relates to new 3-aminopyrazolin-5ones, several processes for their preparation and their use as herbicides.

It has been disclosed that certain amino-substituted heterocyclic compounds containing 5-membered rings, for example certain 2-aminothiazolin-4-ones, such as the compound 2-amino-5-methyl-3-(3-trifluoromethyl-phenyl)-5H-thiazolin-4-one, possess herbicidal properties (cf., for example, U.S. Pat. No. 4,596,595).

However, both the herbicidal activity against problem weeds and the compatibility with important crop plants of these previously known compounds is not entirely satisfactory in all fields of application. New 3-aminopyrazolin-5-ones of the general formula (I)

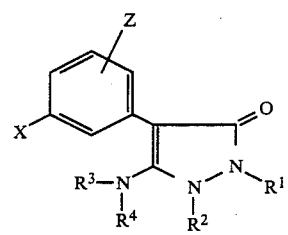
(I)

in which
- $R^1$ stands for alkyl, alkenyl, halogenoalkyl, halogenoalkenyl, alkoxyalkyl, alkylthioalkyl, cycloalkyl, for optionally substituted aralkyl or for optionally substituted aryl,
- $R^2$ stands for hydrogen or alkyl,
- $R^3$ stands for hydrogen or alkyl,
- $R^4$ stands for hydrogen, alkyl, alkenyl, alkinyl, alkoxyalkyl, alkylthioalkyl, alkoxycarbonylalkyl or alkanoyl, or
- $R^3$ and $R^4$ together stand for an alkylene or alkenylene radical, each of which is divalent,
- X stands for halogen, alkyl, alkoxy, alkylthio, halogenoalkyl, halogenoalkoxy or halogenoalkylthio, and
- Z stands for hydrogen, halogen, alkyl, alkoxy, alkylthio, halogenoalkyl, halogenoalkoxy or halogenoalkylthio, and acid addition salts thereof have been found.

In the event that one or more of the substituents $R^2$, $R^3$ or $R^4$ stands for hydrogen, the compounds of the formula (I) can be present in the form of various tautomeric structures:

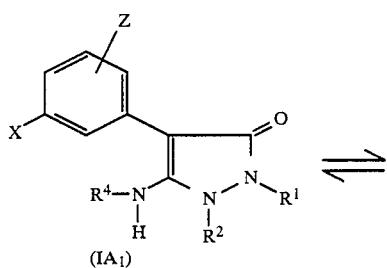
(IA₁)

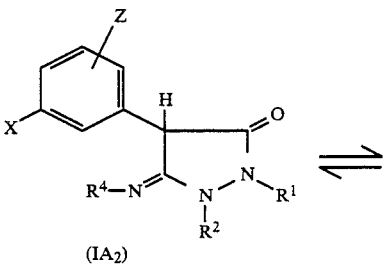
(IA₂)

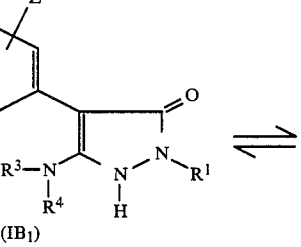
(IA₃)

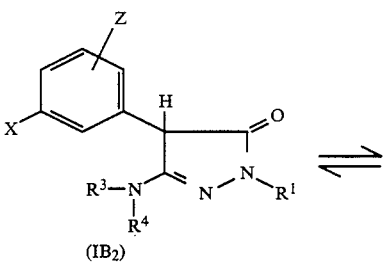
(IB₁)

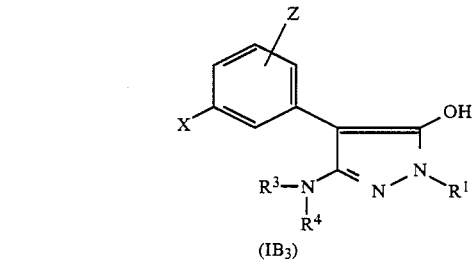
(IB₂)

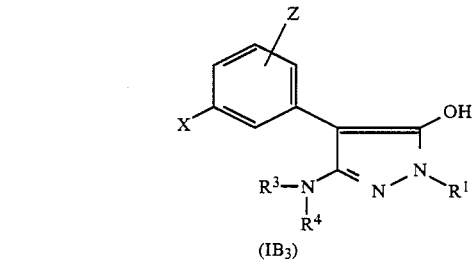
(IB₃)

The invention covers all the tautomeric structures possible.

Furthermore, it has been found that the new 3-aminopyraozlin-5-ones of the general formula (I)

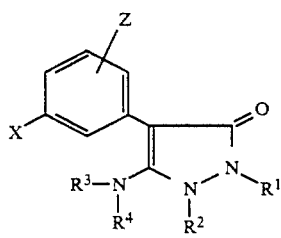
(I)

in which
R¹ stands for alkyl, alkenyl, halogenoalkyl, halogenoalkenyl, alkoxyalkyl, alkylthioalkyl, cycloalkyl, for optionally substituted aralkyl or for optionally substituted aryl,
R² stands for hydrogen or alkyl,
R³ stands for hydrogen or alkyl,
R⁴ stands for hydrogen, alkyl, alkenyl, alkinyl, alkoxyalkyl, alkylthioalkyl, alkoxycarbonylalkyl or alkanoyl, or
R³ and R⁴ together stand for an alkylene or alkenylene radical, each of which is divalent,
X stands for halogen, alkyl, alkoxy, alkylthio, halogenoalkyl, halogenoalkoxy or halogenoalkylthio, and
Z stands for hydrogen, halogen, alkyl, alkoxy, alkylthio, halogenoalkyl, halogenoalkoxy or halogenoalkylthio, and acid addition salts thereof are obtained by one of the processes described below:

(a) 3-aminopyrazolin-5-ones of the formula (Ia)

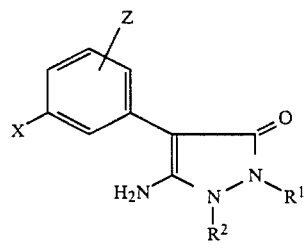
(Ia)

R¹, R², X and Z have the abovementioned meaning, are obtained when iminomalonic ester derivatives of the formula (II)

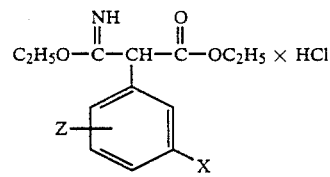
(II)

in which
X and Z have the abovementioned meaning, are reacted with hydrazines of the formula (III)

R¹—NH—NH—R² (III)

in which
R¹ and R² have the abovementioned meaning, or the acid addition salts thereof, if appropriate in the presence of a diluent and if appropriate in the presence of a reaction auxiliary;

(b) 3-aminopyrazolin-5-ones of the formula (Ib)

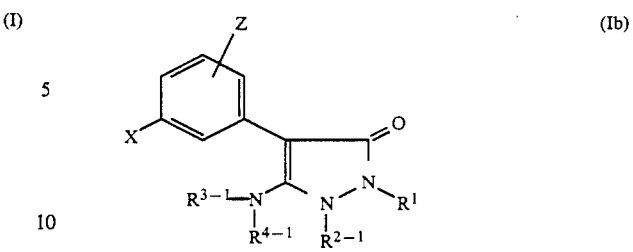
(Ib)

in which at least one of the radicals
R²⁻¹, R³⁻¹ or R⁴⁻¹ stands for alkyl and simultaneously each of the two radicals not concerned stands for hydrogen or alkyl and
R¹, X and Z have the abovementioned meaning, are obtained when the 3-aminopyrazolin-5-ones of the formula (Ia)

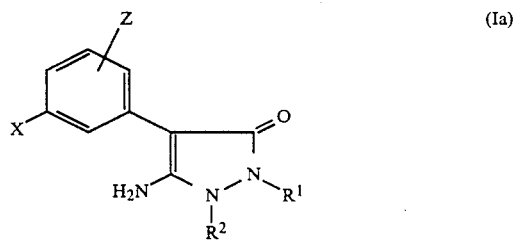
(Ia)

in which
R¹, R², X and Z have the abovementioned meaning, which can be obtained by process (a) are reacted with alkylating agents of the formula (IVa)

R⁵—E¹ (IVa)

in which
R⁵ stands for alkyl and
E¹ stands for an electron-withdrawing leaving group,
if appropriate in the presence of a diluent, if appropriate in the presence of a reaction auxiliary and if appropriate in the presence of a phase-transfer catalyst;

(c) 3-aminopyrazolin-5-ones of the formula (Ic)

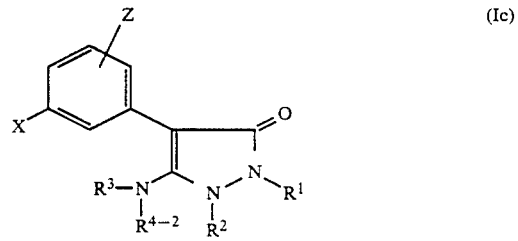
(Ic)

in which
R⁴⁻² stands for alkenyl, alkinyl, alkoxyalkyl, alkylthioalkyl or alkoxycarbonylalkyl and
R¹, R², R³, X and Z have the abovementioned meaning,
are obtained,
when the 3-aminopyrazolin-5-ones of the formula (Iz)

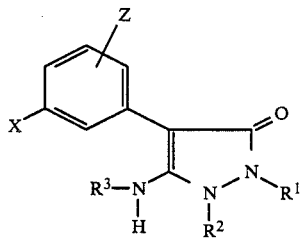
(Iz)

in which
R$^1$, R$^2$, R$^3$, X and Z have the abovementioned meaning,
which can be obtained by processes (a) and (b) are reacted with alkylating agents of the formula (IVb)

R$^{4-2}$—E$^2$ (IVb)

in which
R$^{4-2}$ has the abovementioned meaning and
E$^2$ stands for an electron-withdrawing leaving group,
if appropriate in the presence of a diluent, if appropriate in the presence of a reaction auxiliary and if appropriate in the presence of a phase-transfer catalyst;
(d) 3-aminopyrazolin-5-ones of the formula (Id)

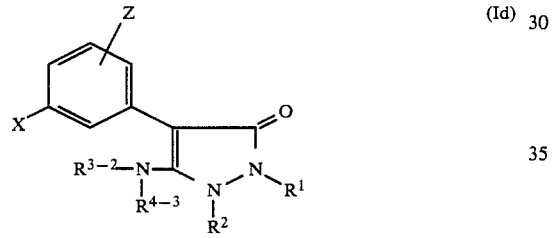
(Id)

in which
R$^{3-2}$ and R$^{4-3}$ together stand for an alkylene or alkenylene radical, each of which is divalent, and
R$^1$, R$^2$, X and Z have the abovementioned meaning,
are obtained when the 3-aminopyrazolin-5-ones of the formula (Ia)

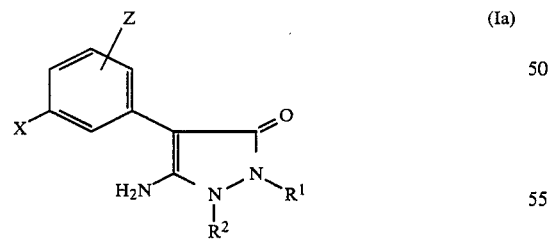
(Ia)

in which
R$^1$, R$^2$, X and Z have the abovementioned meaning, which can be obtained by process (a) are reacted with alkylating agents of the formula (IVc)

E$^3$—A—E$^3$ (IVc)

in which
A stands for an alkylene or alkenylene radical and
E$^3$ stands for an electron-withdrawing leaving group, if appropriate in the presence of a diluent, if appropriate in the presence of a reaction auxiliary and if appropriate in the presence of a phase-transfer catalyst;
(e) 3-aminopyrazolin-5-ones of the formula (Ie)

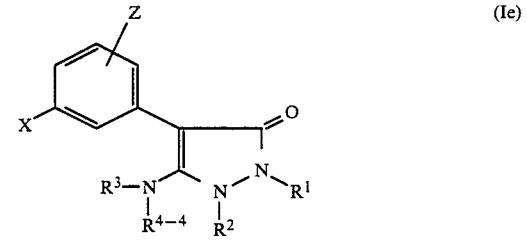
(Ie)

in which
R$^{4-4}$ stands for alkanoyl and
R$^1$, R$^2$, R$^3$, X and Z have the abovementioned meaning,
are obtained when the 3-aminopyrazolin-5-ones of the formula (Iz)

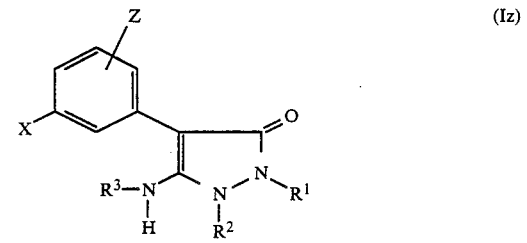
(Iz)

in which
R$^1$, R$^2$, R$^3$, X and Z have the abovementioned meaning,
which can be obtained by process (a) or (b) are reacted with acylating agents of the formula (V)

R$^{4-4}$—E$^4$ (V)

in which
R$^{4-4}$ has the abovementioned meaning and
E$^4$ stands for an electron-withdrawing leaving group,
if appropriate in the presence of a diluent and if appropriate in the presence of a reaction auxiliary; and if appropriate the resultant compounds are then subjected to an addition reaction with an acid.

Finally, it has been found that the new 3-aminopyrazoline-5-ones of the general formula (I) have a very good herbicidal activity Surprisingly, the 3-aminopyrazolin-5-ones of the general formula (I) according to the invention show a considerably better herbicidal activity than the amino-substituted heterocyclic compounds containing 5-membered rings known from the prior art, such as, for example, 2-amino-5-methyl-3-(3-trifluoromethylphenyl)-5H-thiazolin-4-one, which are chemically similar compounds of a similar type of action.

Formula (I) provides a general definition of the 3-aminopyrazolin-5-ones according to the invention. Preferred compounds of the formula (I) are those in which
R$^1$ stands for in each case straight-chain or branched alkyl having 1 to 6 carbon atoms, alkenyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, alkoxyalkyl having 1 to 4 carbon atoms in each of the individual alkyl moieties, or alkylthioalkyl having 1 to 4 carbon atoms in each of the individual alkyl moieties, for cycloalkyl having 3 to 7 carbon atoms, or for aralkyl having 1 to 4 carbon atoms in the alkyl moiety and 6 to 10 carbon atoms in the aryl moiety or aryl having 6 to 10 carbon atoms, in each case optionally monosubstituted or polysubstituted in the aryl moiety by identical or different substituents, suitable aryl substituents in each case being: halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl moieties, and also phenyl which is optionally monosubstituted or polysubstituted by identical or different substituents from the series comprising halogen and/or straight-chain or branched alkyl having 1 to 4 carbon atoms, $R^2$ stands for hydrogen or for straight-chain or branched alkyl having 1 to 4 carbon atoms, $R^3$ stands for hydrogen or for straight-chain or branched alkyl having 1 to 4 carbon atoms, $R^4$ stands for hydrogen or for in each case straight-chain or branched alkyl having 1 to 4 carbon atoms, alkenyl having 3 to 6 carbon atoms, alkinyl having 3 to 6 carbon atoms, alkoxyalkyl, alkylthioalkyl or alkoxycarbonylalkyl, each having 1 to 4 carbon atoms in the individual alkyl moieties, or alkanoyl having 1 to 5 carbon atoms, or $R^3$ and $R^4$ together stand for an alkylene or alkenylene radical, each having 2 to 5 carbon atoms and each being divalent, X stands for fluorine, chlorine, bromine, iodine, for in each case straight-chain or branched alkyl, alkoxy or alkylthio, each having 1 to 4 carbon atoms, or for in each case straight-chain or branched halogenoalkyl, halogenoalkoxy or halogenoalkylthio, each having 1 to 4 carbon atoms and 1 to 9 identical or different halogen atoms, and Z stands for hydrogen, fluorine, chlorine, bromine, iodine, for in each case straight-chain or branched alkyl, alkoxy or alkylthio, each having 1 to 4 carbon atoms, or for in each case straight-chain or branched halogenoalkyl, halogenoalkoxy or halogenoalkylthio, each having 1 to 4 carbon atoms and 1 to 9 identical or different halogen atoms.

Particularly preferred compounds of the formula (I) are those in which $R^1$ stands for methyl, ethyl, n- or i-propyl, n-, i-, s- or t-butyl, for all)1, n- or i-butenyl, for halogenoalkyl having 1 to 2 carbon atoms and 1 to 5 identical or different halogen atoms, in particular fluorine, chlorine or bromine, for allyl, n-butenyl or i-butenyl, in each case optionally monosubstituted or disubstituted by chlorine, for methoxymethyl or methylthiomethyl, for cyclopropyl, cyclopentyl or cyclohexyl, or for phenyl, naphthyl, indenyl, benzyl or phenylethyl, in each case optionally monosubstituted, disubstituted or trisubstituted by identical or different substituents, suitable aryl substituents in each case being: fluorine, chlorine, bromine, cyano, nitro, methyl, ethyl, n- or ipropyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl, ethoximinoethyl or phenyl which is optionally monosubstituted, disubstituted or trisubstituted by identical or different substituents from the series comprising fluorine, chlorine, bromine, methyl and/or ethyl, $R^2$ stands for hydrogen, methyl or ethyl, $R^3$ stands for hydrogen, methyl, ethyl, n- or i-propyl, n-, i-, s- or t-butyl, $R^4$ stands for hydrogen, methyl, ethyl, n- or i-propyl, n-, i-, s- or t-butyl, allyl, propargyl, methoxymethyl, methylthiomethyl, methoxycarbonylmethyl, ethoxycarbonylmethyl, for acetyl or for propionyl, or $R^3$ and $R^4$ together with the nitrogen atom to which they are bonded stand for one of the radicals

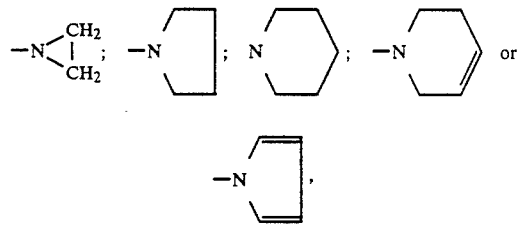

X stands for fluorine, chlorine, bromine, methyl, methoxy, methylthio, trifluoromethyl, trifluoromethoxy or trifluoromethylthio, and Z stands for hydrogen, fluorine, chlorine, bromine, methyl, methoxy, methylthio, trifluoromethyl, trifluoromethoxy or trifluoromethylthio.

Other preferred compounds according to the invention are addition products of acids and those 3-aminopyrazolin-5-ones of the formula (I) in which the substituents $R^1$, $R^2$, $R^3$, $R^4$, X and Z have the meanings which have already been mentioned as being preferred for these substituents.

The acids which can be subjected to the addition reaction preferably include hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Very particularly preferred compounds of the formula (I) are those in which $R^1$ stands for methyl, ethyl, n-propyl, i-propyl or n-butyl, for allyl, for cyclohexyl, or for benzyl or phenyl, in each case optionally monosubstituted, disubstituted or trisubstituted by identical or different substituents, suitable substituents being: fluorine, chlorine, bromine, nitro, methyl, methoxy, ethyl or trifluoromethyl, $R^2$ stands for methyl, $R^3$ stands for hydrogen, methyl, ethyl, n- or i-propyl, $R^4$ stands for hydrogen, methyl, ethyl, n- or i-propyl, for allyl or propargyl, X stands for fluorine, chlorine or trifluoromethyl and Z stands for hydrogen or fluorine.

In addition to the compounds mentioned in the preparation examples, the following 3-aminopyrazolin-5-ones of the general formula (I) may be mentioned individually:

TABLE 1

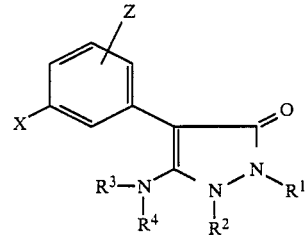

(I)

| $R^1$ | $R^2$ | $R^3$ | $R^4$ | X / Z-phenyl |
|---|---|---|---|---|
| 4-Cl-C₆H₄ | CH₃ | H | CH₃ | 3-CF₃-C₆H₄ |
| 3-Cl-C₆H₄ | CH₃ | H | —CH₂—CH=CH₂ | 3-CF₃-C₆H₄ |
| 2-Cl-C₆H₄ | CH₃ | CH₃ | CH₃ | 3-CF₃-C₆H₄ |
| 4-CH₃-C₆H₄ | CH₃ | H | CH₃ | 3-CF₃-C₆H₄ |
| 4-CH₃O-C₆H₄ | CH₃ | H | CH₃ | 3-CF₃-C₆H₄ |
| 3,4-Cl₂-C₆H₃ | CH₃ | H | CH₃ | 3-CF₃-C₆H₄ |
| 4-F-C₆H₄ | CH₃ | H | CH₃ | 3-CF₃-C₆H₄ |
| 3,4-F₂-C₆H₃ | CH₃ | H | CH₃ | 3-CF₃-C₆H₄ |
| 3-F-C₆H₄ | CH₃ | H | CH₃ | 3-CF₃-C₆H₄ |
| 2-F-C₆H₄ | CH₃ | H | CH₃ | 3-CF₃-C₆H₄ |

TABLE 1-continued (I)

| $R^1$ | $R^2$ | $R^3$ | $R^4$ | X / Z-phenyl |
|---|---|---|---|---|
| 3,5-Cl₂-C₆H₃ | CH₃ | H | CH₃ | 3-CF₃-C₆H₄ |
| 3-NO₂-C₆H₄ | CH₃ | H | CH₃ | 3-CF₃-C₆H₄ |
| 2-NO₂-C₆H₄ | CH₃ | H | CH₃ | 3-CF₃-C₆H₄ |
| 3,5-(NO₂)₂-C₆H₃ | CH₃ | H | CH₃ | 3-CF₃-C₆H₄ |
| 3-CH₃-C₆H₄ | CH₃ | H | CH₃ | 3-CF₃-C₆H₄ |
| 2-CH₃-C₆H₄ | CH₃ | H | CH₃ | 3-CF₃-C₆H₄ |
| 3,5-(CH₃)₂-C₆H₃ | CH₃ | H | CH₃ | 3-CF₃-C₆H₄ |
| 3,5-F₂-C₆H₃ | CH₃ | H | CH₃ | 3-CF₃-C₆H₄ |
| C₆H₅-CH₂— | CH₃ | H | CH₃ | 3-CF₃-C₆H₄ |
| 2-Cl-C₆H₄-CH₂— | CH₃ | H | CH₃ | 3-CF₃-C₆H₄ |
| 2-F-C₆H₄-CH₂— | CH₃ | H | CH₃ | 3-CF₃-C₆H₄ |

TABLE 1-continued

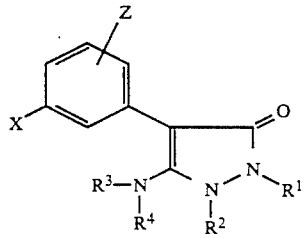

If, for example, ethyl 3-ethoxy-3-imino-2-(3-trifluoromethyl-phenyl)-propionate hydrochloride and phenylhydrazine are used as starting substances, the course of the reaction of process (a) according to the invention may be represented by the following equation:

If, for example, 3-amino-1-phenyl-4-(3-trifluoromethylphenyl)-2H-pyrazolin-5-one and dimethyl sulphate are used as starting substances, the course of the reaction of process (b) according to the invention may be represented by the following equation:

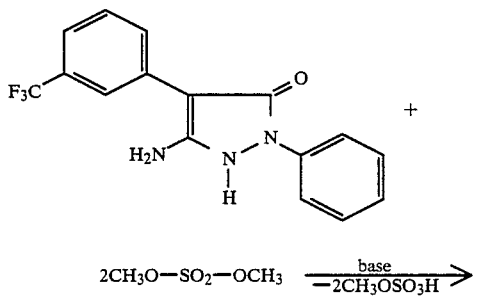

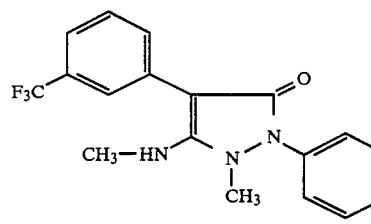

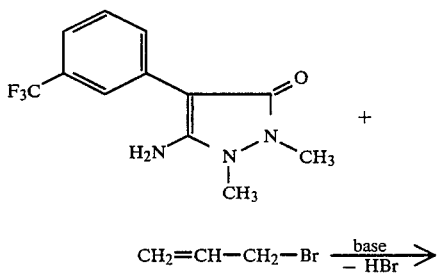

If, for example, 3-amino-1,2-dimethyl-4-(3-trifluoromethylphenyl)-Δ³-pyrazolin-5-one and allyl bromide are used as starting substances, the course of the reaction of process (c) according to the invention may be represented by the following equation:

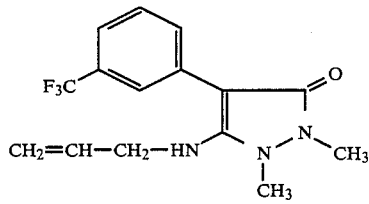

If, for example, 3-amino-1,2-dimethyl-4-(3-trifluoromethylphenyl)-Δ³-pyrazolin-5-one and 1,4-dibromobuta-1,3-diene are used as starting substances, the course of the reaction of process (d) according to the invention may be represented by the following equation:

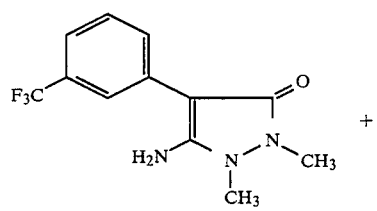

-continued

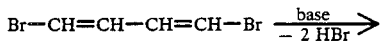

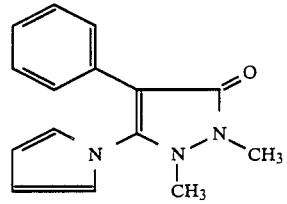

If, for example, 3-amino-2-methyl-1-phenyl-4-(3-trifluoromethylphenyl)-Δ³-pyrazolin-5-one and acetic anhydride are used as starting substances, the course of the reaction of process (e) according to the invention may be represented by the following equation:

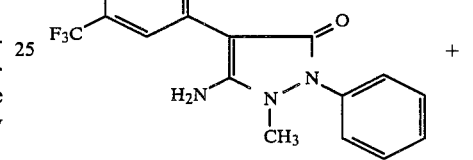

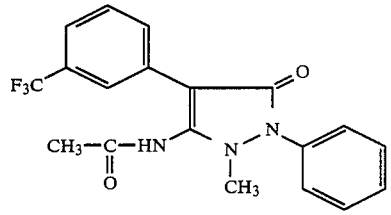

Formula (II) provides a general definition of the iminomalonic ester derivatives required as starting substances for carrying out process (a) according to the invention. In this formula (II), X and Z preferably stand for those radicals which have already been mentioned in connection with the description of the substances of the formula (I) according to the invention as being preferred for these substituents.

The iminomalonic ester derivatives of the formula (II) were hitherto unknown.

They are obtained when phenylacetonitrile derivatives of the formula (VI)

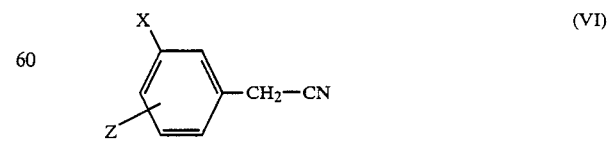

in which
X and Z have the abovementioned meaning, are initially reacted, in a first step, with diethyl carbonate of the formula (VII)

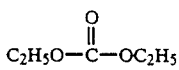

(VII)

at temperatures between 20° C. and 120° C., if appropriate in the presence of a diluent, such as, for example ethanol, and if appropriate in the presence of a base, such as, for example, sodium ethoxide (in this context, also cf. Organic Syntheses Coll. Vol. IV; p. 461 [1963]), and, in a 2nd step, the resulting 2-arylcyanoacetic esters of the formula (VIII)

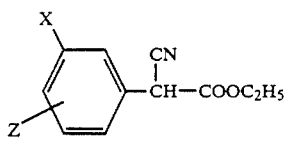

(VIII)

in which

X and Z have the abovementioned meaning, are reacted with ethanol and hydrogen chloride at temperatures between −20° C. and +20° C., if appropriate in the presence of a diluent, such as, for example, diethyl ether (cf., for example, Helv. Chim. Acta 43, 1727-1733 [1960]).

The phenylacetonitrile derivatives of the formula (VI) are known or can be obtained in analogy with known processes (cf., for example, DE-OS (German Published Specification) 2,160,119; GB 1,238,522; DE-OS (German Published Specification) 1,200,970; U.S. Pat. No. 3,476,790; U.S. Pat. No. 3,277,106).

Diethyl carbonate of the formula (VII) is a generally known compound of organic chemistry (cf., for example, U.S. Pat. No. 3,415,867).

Formula (III) provides a general definition of the hydrazines furthermore required as starting substances for carrying out process (a) according to the invention. In this formula (III), $R^1$ and $R^2$ preferably stand for those radicals which have already been mentioned in connection with the description of the substances of the formula (I) according to the invention as being preferred for these substituents.

Particularly preferred acid addition salts of hydrazines of the formula (III) are hydrochlorides or hydroacetates.

The hydrazines of the formula (III) and their acid addition salts are generally known compounds of organic chemistry.

Formula (Ia) provides a general definition of the 3-aminopyrazolin-5-ones required as starting substances for carrying out processes (b) and (d) according to the invention. In this formula (Ia), $R^1$, $R^2$, X and Z preferably stand for those radicals which have already been mentioned in connection with the description of the substances of the formula (I) according to the invention as being preferred for these substituents.

The 3-aminopyrazolin-5-ones of the formula (Ia) are compounds according to the invention and can be obtained with the aid of process (a) according to the invention.

Formula (IVa) provides a general definition of the alkylating agents furthermore required as starting substances for carrying out process (b) according to the invention. In this formula (IVa), $R^5$ preferably stands for straight-chain or branched alkyl having 1 to 4 carbon atoms, in particular for methyl, ethyl and n- or i-propyl. $E^1$ preferably stands for halogen, in particular for chlorine, bromine or iodine, or for alkoxysulphonyloxy, such as, for example, methoxysulphonyloxy or ethoxysulphonyloxy, or for optionally substituted arylsulphonyloxy, such as, for example, p-toluenesulphonyloxy.

The alkylating agents of the formula (IVa) are generally known compounds of organic chemistry.

Formula (Iz) provides a general definition of the 3-amino-pyrazolin-5-ones required as starting substances for carrying out processes (c) and (e) according to the invention. In this formula (Iz), $R^1$, $R^2$, $R^3$, X and Z preferably stand for those radicals which have already been mentioned in connection with the description of the substances of the formula (I) according to the invention as being preferred for these substituents.

The 3-aminopyrazolin-5-ones of the formula (Iz) are compounds according to the invention and can be obtained with the aid of processes (a) and (b) according to the invention.

Formula (IVb) provides a general definition of the alkylating agents furthermore required as starting substances for carrying out process (c) according to the invention. In this formula (IVb), $R^{+2}$ preferably stands for alkenyl having 3 to 6 carbon atoms, for alkinyl having 3 to 6 carbon atoms or for alkoxyalkyl, alkylthioalkyl or alkoxycarbonylalkyl, each having 1 to 4 carbon atoms in the individual alkyl moieties; in particular, $R^{+2}$ stands for allyl, propargyl, methoxymethyl, methylthiomethyl, methoxycarbonylmethyl or ethoxycarbonylmethyl. $E^2$ preferably stands for halogen, in particular for chlorine, bromine or iodine.

The alkylating agents of the formula (IVb) are generally known compounds of organic chemistry.

Formula (IVc) provides a general definition of the alkylating agents furthermore required as starting substances for carrying out process (d) according to the invention. In this formula (IVc), A preferably stands for an alkylene or alkenylene radical, each having 2 to 5 carbon atoms and each being divalent, in particular for one of the radicals —CH$_2$—CH$_2$—; —CH$_2$—CH$_2$—CH$_2$—CH$_2$—; —CH$_2$—CH$_2$—CH$_2$—CH$_2$—CH$_2$—; —CH$_2$—CH=CH—CH$_2$—CH$_2$—or —CH=CH—CH=CH—. $E^3$ preferably stands for halogen, in particular bromine.

The alkylating agents of the formula (IVc) are generally known compounds of organic chemistry.

Formula (V) provides a general definition of the acylating agents furthermore required as starting substances for carrying out process (e) according to the invention. In this formula (V), $R^{+4}$ preferably stands for straight-chain or branched alkanoyl having 1 to 5 carbon atoms, in particular for acetyl or propionyl. $E^4$ preferably stands for halogen, in particular for chlorine or bromine, or for a radical $R^{+4}$—CO—O —, $R^{+4}$ preferably standing for the abovementioned radicals.

The acylating agents of the formula (V) are also generally known compounds of organic chemistry.

Suitable diluents for carrying out process (a) according to the invention are inert organic solvents. Alcohols, in particular methanol or ethanol, or organic acids, such as, for example, acetic acid, are particularly preferably used.

Process (a) according to the invention is preferably carried out in the presence of a suitable reaction auxiliary. Preferably, aprotic bases are used, suitable substances being in particular alkali metal alkoxides, such as, for example, sodium methoxide or sodium ethoxide.

When carrying out process (a) according to the invention, the reaction temperatures may be varied within a relatively wide range. In general, the process is carried out at temperatures between −20° C. and +50° C., preferably at temperatures between 0° C. and 30° C.

For carrying out process (a) according to the invention, 1.0 to 1.5 moles, preferably 1.0 to 1.2 moles, of hydrazine of the formula (III) and if appropriate 1.0 to 5.0 moles, preferably 1.0 to 3.0 moles, of reaction auxiliary are generally employed per mole of iminomalonic ester derivative of the formula (II). It may in some cases be advantageous to carry out the reaction in the presence of a dry inert gas atmosphere of nitrogen, and to maintain the pH of the reaction mixture at the point of neutrality. If necessary, the pH can be corrected by the addition of alkoxide or glacial acetic acid. The reaction is carried out and the reaction products are worked up and isolated by generally customary methods (cf. also preparation examples).

Suitable diluents for carrying out processes (b), (c) or (d) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran and ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or alcohols, such as methanol or ethanol.

Processes (b), (c) or (d) according to the invention are preferably carried out in the presence of a suitable reaction auxiliary. Suitable compounds are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

If appropriate, it is also possible for processes (b), (c) or (d) according to the invention to be carried out in a two-phase system, such as, for example, water/toluene or water/dichloromethane, if appropriate in the presence of a phase-transfer catalyst. Catalysts which may be mentioned as examples are: tetrabutylammonium iodide, tetrabutylammonium bromide, tributyl-methyl-phophonium bromide, trimethyl-$C_{13}/C_{15}$-alkylammonium chloride, dibenzyldimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride and trimethylbenzylammonium chloride.

When carrying out processes (b), (c) or (d) according to the invention, the reaction temperatures may be varied within a relatively wide range. In general, the processes are carried out at temperatures between 0° C. and 100° C., preferably at temperatures between 20° C. and 80° C.

For carrying out process (b) according to the invention, 1.0 to 5.0 moles, preferably 1.0 to 3.0 moles, of alkylating agent of the formula (IVa) and if appropriate 1.0 to 5.0 moles, preferably 1.0 to 3.0 moles, of reaction auxiliary, and if appropriate 0.01 to 1.0 mole of phase-transfer catalyst are generally employed per mole of 3-amino-pyrazolin-5-one of the formula (Ia).

Depending on the amount of alkylating agent of the formula (IVa) employed, mono-, di- or trialkylated compounds of the formula (Ib) are obtained.

Depending on the type of the reaction conditions chosen, it is possible to specifically influence the site of alkylation if the alkylating agent of the formula (IVa) is employed in deficiency. Thus, if, for example, a protic solvent is chosen, the ring nitrogen is preferentially alkylated, whereas under reaction conditions free from water or in the case of phase-transfer catalysis, alkylation of the exocyclic 3-amino group takes place preferentially. If any product mixtures occur, they can be separated using methods of chromatography, and any O-alkylated compounds formed in side reactions may be separated off using the same methods.

The reaction is carried out and the reaction products are worked up and isolated by generally customary methods (also cf. preparation examples).

For carrying out process (c) according to the invention, 1.0 to 3.0 moles, preferably 1.0 to 2.0 moles of alkylating agent of the formula (IVb) and if appropriate 1.0 to 3.0 moles, preferably 1.0 to 2.0 moles, of reaction auxiliary are generally employed per mole of 3-aminopyrazolin-5-one of the formula (Iz). The reaction is carried out and the reaction products are worked up and isolated by generally customary methods.

For carrying out process (d) according to the invention, 0.3 to 0.7 mole, preferably 0.45 to 0.5 mole, of alkylating agent of the formula (IVc) and if appropriate 1.0 to 3.0 moles, preferably 1.0 to 2.0 moles, of reaction auxiliary are generally employed per mole of 3-aminopyrazolin-5-one of the formula (Ia). The reaction is carried out and the reaction products are worked up and isolated by generally customary Suitable diluents for carrying out process (e) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran and ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate.

Process (e) according to the invention is preferably carried out in the presence of a suitable reaction auxiliary. Suitable substances are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (e) according to the invention, the reaction temperatures may be varied within a relatively wide range. In general, the process is 5 carried out at temperatures between −20° C. and +150° C., preferably at temperatures between 0° C. and 120° C.

For carrying out process (e) according to the invention, 1.0 to 3.0 moles, preferably 1.0 to 2.0 moles, of acylating agent of the formula (V) and if appropriate 1.0 to 3.0 moles, preferably 1.0 to 2.0 moles, of reaction auxiliary are generally employed per mole of 3-aminopyrazolin-5-one of the formula (Iz).

The reaction is carried out and the reaction products are worked up and isolated by generally customary methods.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtering off, and if necessary purified by washing with an inert organic solvent.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulae, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzthiazolyl)-N,N'-dimethylurea (METABENZTHIAZURON) for combating weeds in cereals; 4-amino-3-methyl-6-phenyl-1,2,4-triazin-5'(4H)-one (META-MITRON) for combating weeds in sugarbeets and 4-amino-6-(1,1-dimethylethyl)-3-methylthio-1,2,4-triazin-5(4H)-one (METRIBUZIN) for combating weeds in soy beans. Surprisingly, some mixtures also show a synergistic action.

Mixtures with other known active compounds, such as fungicides, insecticides, acaricides, nematicides, bird repellents plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

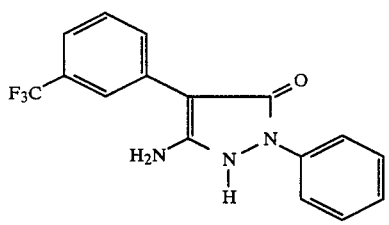

(Process (a))

Under a dry nitrogen atmosphere, and at 0° C. to 5° C., 59.4 g (1.1 moles) of sodium methoxide in 200 ml of methanol are added dropwise, with stirring and over the course of one hour, to 339.5 g (1.0 mole) of ethyl 2-(1-ethoxyformimidoyl)-2-(3-trifluoromethylphenyl)-acetate hydrochloride in 800 ml of dry methanol 108 g (1.0 mole) of phenylhydrazine in 150 ml of methanol are then added dropwise with stirring and over the course of 30 minutes, likewise at 0° C. to 5° C., the pH of the mixture is then checked and, if necessary, corrected to pH 7 using methanolic sodium methoxide solution or glacial acetic acid. The mixture is stirred for 2 hours at 0° C. to 5° C. and for 16 hours at room temperature, the reaction batch is then poured into 2 l of water, the mixture is extracted with 1 l of dichloromethane, and the organic phase is washed with 1 l of water, the product precipitating from the organic phase. The phases are separated, the product is filtered off by suction and washed with 100 ml of dichloromethane, and the resulting solid is dried.

268 g (84% of theory) of 3-amino-1-phenyl-4-(3-trifluoromethylphenyl)-2H(4H)-pyrazolin-5-one of melting point 187° C. are obtained.

Preparation of the starting compound

Example (II-1)

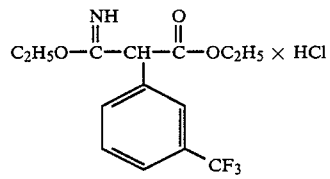

Under a dry nitrogen atmosphere and at 0° C. to 5° C., 46 g (1.0 mole) of ethanol are added to 257 g (1.0 mole) of ethyl 2-(3-trifluoromethylphenyl)-cyanoacetate in 1 l of diethyl ether, dry hydrogen chloride gas is then passed in to saturation, the mixture is stirred at 0° C. to 5° C. for a further 30 minutes and evaporated in vacuo, and the residue is stirred with ether and filtered off by suction.

340 g (100% of theory) of ethyl 2-(1-ethoxyformimoyl)-2-(3-trifluoromethylphenyl)-acetate hydrochloride are obtained and is immediately reacted further without additional purification.

Example (VIII-1)

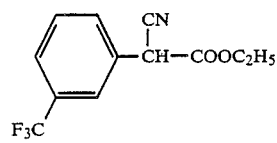

Under a dry nitrogen atmosphere and at 70° C., 600 ml (5.0 moles) of diethyl carbonate and 185 g (1.0 mole) of 3-trifluoromethylbenzyl cyanide are added to a solution of 23.9 g (1.04 moles) of sodium in 600 ml of ethanol. The ethanol is then distilled off under reduced pressure, and, simultaneously, 160 ml of absolute toluene are added dropwise. When the distillation is complete, 600 ml of water are added, the mixture is acidified using 80 ml of glacial acetic acid, the organic phase is separated off, washed with water, dried over sodium sulphate and evaporated in vacuo, and the residue is distilled under a high vacuum.

228 g (88.7% of theory) of ethyl 2-(3-trifluoromethylphenyl)-cyanoacetate of boiling point 105° C. to 111° C. at 0.1 mbar are obtained.

Example 2

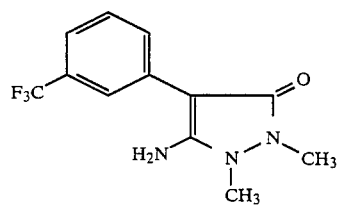

(Process (a))

108 g (2.0 moles) of sodium methoxide in 250 ml of methanol are added to 133 g (1.0 mole) of N,N'-dimethylhydrazine dihydrochloride in 250 ml of methanol, the mixture is stirred at room temperature for 30 minutes and filtered by suction, and the filtrate is added dropwise to a solution of 339.5 g (1.0 mole) of ethyl 2(1-ethoxyformimidoyl)-2-(3-trifluoromethylphenyl)-acetate hydrochloride in 500 ml of methanol under a dry nitrogen atmosphere and at 0° C. to 5° C. with stirring and cooling, to which solution 59.4 g (1.1 moles) of sodium methoxide in 200 ml of methanol have previously been added dropwise, with stirring and over the course of one hour, likewise under a dry nitrogen atmosphere and at 0° C. to 5° C. When the addition is complete, the pH is adjusted to neutrality using sodium methoxide or glacial acetic acid, the mixture is stirred for 4 hours at 0° C. to 5° C. and then for 16 hours at room temperature. The reaction batch is then poured into 2,000 ml of water, the mixture is extracted with 600 ml of dichloromethane, and the organic phase is dried over sodium sulphate and evaporated in vacuo. The residue is stirred with dichloromethane/petroleum ether (1 : 1), filtered off by suction and dried.

81 g (30% of theory) of 3-amino-1,2-dimethyl-4-(3-trifluoromethylphenyl)-Δ³-pyrazolin-5-one of melting point 156° C.–157° C. are obtained.

Example 3

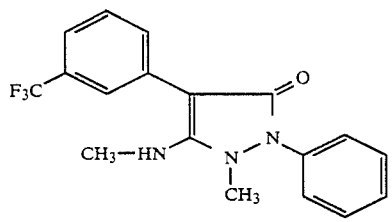

(Process (b))

15 ml of 45% strength aqueous sodium hydroxide solution and 0.25 g of tributylbenzylammonium bromide are added to 15.95 g (0.05 mole) of 3-amino-1-phenyl-4-(3-trifluoromethylphenyl)-2H(4H)-pyrazolin-5-one in 375 ml of dichloromethane, and 6.3 g (0.05 mole) of dimethyl sulphate in 50 ml of dichloromethane are then added dropwise with stirring and at room temperature to the reaction mixture. When the addition is complete, the mixture is stirred for 16 hours at room temperature, 250 ml of water are then added, the organic phase is separated off, washed with water, dried over sodium sulphate and evaporated in vacuo, and the residue is purified by chromatography on silica gel (mobile phase: petroleum ether/ethyl acetate 7:3).

5.0 g (30% of theory) of 2-methyl-3-methylamino-1-phenyl-4-(3-trifluoromethylphenyl)-Δ³-pyrazolin-5-one of melting point 205° C. to 206° C. are obtained.

Example 4

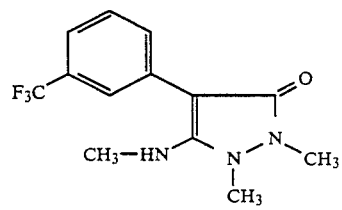

(Process (b))

3 ml of 45% strength aqueous sodium hydroxide solution and 0.05 g of tributylbenzylammonium bromide are added to 2.71 g (0.01 mole) of 3-amino-1,2-dimethyl-4-(3-trifluoromethylphenyl)-Δ³-pyrazolin-5-one in 75 ml of dichloromethane, 1.26 g (0.01 mole) of dimethyl sulphate in 10 ml of dichloromethane are then added dropwise and with stirring to the mixture at room temperature, the mixture is stirred for 16 hours at room temperature when the addition is complete, 10 ml of water are added, the organic phase is separated off, washed with water, dried over sodium sulphate and evaporated in vacuo, and the residue is purified by chromatography on silica gel (mobile phase: dichloromethane/methanol 40:1).

1.4 g (49% of theory) of 1,2-dimethyl-3-methyl amino-4-(3-trifluoromethylphenyl-Δ³-pyrazolin-5-one of melting point 152° C.–153° C. are obtained.

Example 5

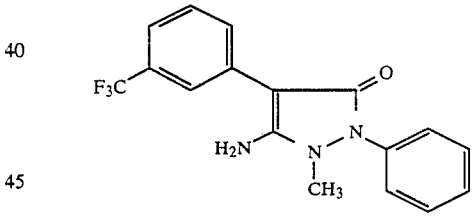

(Process (b))

At the reflux temperature, 12.5 g (0.1 mole) of dimethyl sulphate are added dropwise and with stirring to 8.0 g (0.1 mole) of 45% strength aqueous sodium hydroxide solution and 32.0 g (0.1 mole) of 3-amino-1-phenyl-4-(3-trifluoromethylphenyl)-2H(4H)-pyrazolin-5-one in 50 ml of methanol. The batch is then allowed to cool to room temperature with stirring and is evaporated in vacuo. The residue is stirred with warm water, filtered off by suction, stirred with 30 ml of dichloromethane, again filtered off by suction and dried.

13 g (40% of theory) of 3-amino-2-methyl-1-phenyl-4-(3-trifluoromethylphenyl)-Δ³-pyrazolin-5-one of melting point >250° C. are obtained.

The following 3-aminopyrazolin-5-ones of the general formula (I) are obtained in a corresponding manner and in accordance with the general instructions for the preparation:

TABLE 2

Structure (I): 3-aryl-4-aryl-5-amino-pyrazolin-3-one with substituents R¹ (N1), R² (N2), R³R⁴N- (at C5), X and Z on aryl ring.

| Example No. | R¹ | R² | R³ | R⁴ | X/Z-aryl | Melting point (°C.) |
|---|---|---|---|---|---|---|
| 6 | 3-Cl-C₆H₄ | H | H | H | 3-CF₃-C₆H₄ | 193–194 |
| 7 | C₆H₅ | CH₃ | CH₃ | CH₃ | 3-CF₃-C₆H₄ | 167–168 |
| 8 | CH₃ | CH₃ | CH₃ | CH₃ | 3-CF₃-C₆H₄ | 93–94 |
| 9 | 3-Cl-C₆H₄ | CH₃ | H | CH₃ | 3-CF₃-C₆H₄ | 205–206 |
| 10 | 4-Cl-C₆H₄ | CH₃ | H | H | 3-CF₃-C₆H₄ | >250 |
| 11 | CH₃ | CH₃ | H | -C(O)-CH₃ | 3-CF₃-C₆H₄ | 185–186 |
| 12 | 2-F-C₆H₄ | H | H | H | 3-CF₃-C₆H₄ | 219 |
| 13 | 3-F-C₆H₄ | H | H | H | 3-CF₃-C₆H₄ | 198 |
| 14 | 4-F-C₆H₄ | H | H | H | 3-CF₃-C₆H₄ | 164 |

TABLE 2-continued $$\text{(I)}$$

Structure: pyrazolinone of formula (I) with substituents as shown in header.

| Example No. | R¹ | R² | R³ | R⁴ | Aryl (X, Z) | Melting point (°C.) |
|---|---|---|---|---|---|---|
| 15 | 4-F-C₆H₄− | CH₃ | H | CH₃ | 3-CF₃-C₆H₄− | 195–196 |
| 16 | 4-F-C₆H₄− | CH₃ | CH₃ | CH₃ | 3-CF₃-C₆H₄− | 195–196 |
| 17 | 2-F-C₆H₄− | CH₃ | H | H | 3-CF₃-C₆H₄− | 230–231 |
| 18 | 3-F-C₆H₄− | CH₃ | H | H | 3-CF₃-C₆H₄− | 244–246 |
| 19 | 4-F-C₆H₄− | CH₃ | H | H | 3-CF₃-C₆H₄− | >250 |
| 20 | 2-F-C₆H₄− | CH₃ | H | CH₃ | 3-CF₃-C₆H₄− | 187 |
| 21 | 3-F-C₆H₄− | CH₃ | H | CH₃ | 3-CF₃-C₆H₄− | 191 |
| 22 | 4-Cl-C₆H₄− | CH₃ | CH₃ | CH₃ | 3-CF₃-C₆H₄− | 156 |

TABLE 2-continued (I)

[Structure: phenyl ring with Z and X substituents attached to pyrazolone ring with R1, R2, R3, R4 substituents on nitrogens]

| Example No. | R1 | R2 | R3 | R4 | phenyl (X, Z) | Melting point (°C.) |
|---|---|---|---|---|---|---|
| 23 | 3-F-phenyl | | CH3 | CH3 | CH3 | 3-CF3-phenyl | 149 |
| 24 | 4-Cl-phenyl | | CH3 | H | CH3 | 3-CF3-phenyl | 157 |
| 25 | 3-Cl-phenyl | | CH3 | H | H | 3-CF3-phenyl | 235 |
| 26 | 4-Cl-phenyl | | H | H | H | 3-CF3-phenyl | 178–179 |

Use Example

In the following use example, the compound shown below was employed as the comparison substance:

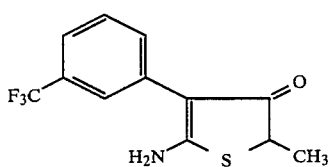

(A)

2-amino-5-methyl-3-(3-trifluoromethyl-phenyl)-5H-thiazolin-4-one (disclosed in U.S. Pat. No. 4,596,595/Example 3).

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the compounds of Preparation Examples (3), (9), (15), (20), (21) and (22), for example, show a clearly superior activity as compared with the prior art.

It will be appreciated that the instant specification and claims are set forth by way of illustration and not limitation, and that various modifications and changes may be made without departing from the spirit and scope of the present invention.

What is claimed is:

1. An iminomalonic ester derivative of the formula

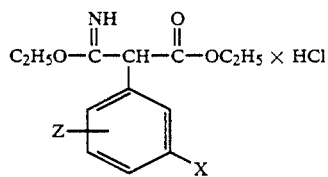 (II)

in which
X stands for halogen, alkyl, alkoxy, alkylthio, halogenoalkyl, halogenoalkoxy or halogenoalkylthio, and
Z stands for hydrogen, halogen, alkyl, alkoxy, alkylthio, halogenoalkyl, halogenoalkoxy or halogenoalkylthio.

* * * * *

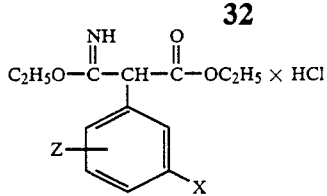 (II)

in which
X stands for halogen, alkyl, alkoxy, alkylthio, halogenoalkyl, halogenoalkoxy or halogenoalkylthio, and
Z stands for hydrogen, halogen, alkyl, alkoxy, alkylthio, halogenoalkyl, halogenoalkoxy or halogenoalkylthio.

* * * * *